US006436708B1

(12) United States Patent
Leone et al.

(10) Patent No.: US 6,436,708 B1

(45) Date of Patent: Aug. 20, 2002

(54) DELIVERY SYSTEM FOR GENE THERAPY TO THE BRAIN

(76) Inventors: Paola Leone, 751 E. Passyunk Ave., Philadelphia, PA (US) 19107; Matthew J. During, 221 12th St., #6055, Philadelphia, PA (US) 19147; Frank L. Sorgi, 1215 Pickett St., Sonoma, CA (US) 95476

( * ) Notice: Subject to any disclaimer, the term of this patent is extended or adjusted under 35 U.S.C. 154(b) by 0 days.

(21) Appl. No.: 09/202,564

(22) PCT Filed: Apr. 17, 1998

(86) PCT No.: PCT/US98/07559

§ 371 (c)(1),
(2), (4) Date: Feb. 8, 1999

(87) PCT Pub. No.: WO98/46273

PCT Pub. Date: Oct. 22, 1998

Related U.S. Application Data

(60) Provisional application No. 60/045,236, filed on Apr. 17, 1997, and provisional application No. 60/050,617, filed on Jun. 24, 1997.

(51) Int. Cl.[7] .......................... C12N 15/88; C12N 15/00

(52) U.S. Cl. ...................... 435/458; 514/44; 435/320.1; 435/455; 424/450

(58) Field of Search ............................... 435/320.1, 91, 435/455, 458, 450; 424/450, 93.2; 514/44

(56) References Cited

U.S. PATENT DOCUMENTS

| | | | | | |
|---|---|---|---|---|---|
| 4,866,042 | A | * | 9/1989 | Neuwelt | 514/44 |
| 5,578,475 | A | | 11/1996 | Jessee | |
| 5,627,159 | A | | 5/1997 | Shih et al. | |
| 5,679,635 | A | * | 10/1997 | Matalon | 435/6 |
| 5,962,429 | A | * | 10/1999 | Welsh et al. | 514/44 |
| 6,022,874 | A | * | 2/2000 | Wheeler | 514/247 |
| 6,041,252 | A | * | 3/2000 | Walker et al. | 604/20 |
| 6,071,533 | A | * | 6/2000 | Papahadjopoulos et al. | 424/450 |
| 6,086,913 | A | * | 7/2000 | Tam et al. | 424/450 |
| 6,096,716 | A | * | 8/2000 | Hayes et al. | 514/44 |
| 6,180,613 | B1 | * | 1/2001 | Kaplitt et al. | 514/44 |

FOREIGN PATENT DOCUMENTS

| | | | |
|---|---|---|---|
| WO | WO 95/34670 | * | 12/1995 |
| WO | WO 96/22765 | | 1/1996 |

OTHER PUBLICATIONS

Barber, "Hospital to pioneer gene therapy for fatal brain disorder," *The New Zealand Harold* Mar. 6, 1996.

*During & Tipene–Hook, "Gene therapy—What is it?" *New Ethicals* 34(5):57–65 (1997).

Adachi, et al., "Protracted form of spongy degeneration of the central nervous system (van Bogaert and Bertrand type)," *Neurology* 18:1084–92 (1968).

Ball, "The Gesell Developmental Schedules: Arnold Gesell (1880–1961)," *Journal of Abnormal Child Psychology* 5:233–9 (1977).

Banerji, et al., "A lymphocyte–specific cellular enhancer is located downstream of the joining region in immunoglobulin heavy chain genes," *Cell* 33:729–740 (1983).

Behar, et al., Analysis of macromolecule resonances in 1 H NMR spectra of human brain, *Magn Reson Med* 32:294–302 (1994).

Canavan, "Schilder's encephalitis periaxialis diffusa," *Arch Neurol Psychiatry* 25:299–308 (1931).

Clarenc, et al., "Delivery of antisense oligonucleotides by poly(L–lysine) conjugation and liposome encapsulation," *Anticancer Drug Design* 8:81–94 (1993).

Davidson, et al., "A model system for in vivo gene transfer into the central nervous system using an adenoviral vector," *Nat Genet* 3:219–223 (1993).

During, et al., "Long–term behavioral recovery in parkinsonian rats by an HSV vector expressing tyrosine hydroxylase," *Science* 266:1399–1403 (1994).

Felgner, et al., "Cationic liposome–mediated transfection," *Nature* 337:387–388 (1989).

Felgner, et al., "Lipofection: a highly efficient, lipid–mediated DNA–transfection procedure," *Proc. Natl. Acad. Sci.* USA 84:7413–7417 (1987).

Kaul, et al., "Canavan disease: Genomic organization and localization of Human ASPA to 17p13–ter and conservation of the ASPA gene during evolution," *Genomics* 21:364–370 (1994).

Kaul, et al., "Canavan disease: Mutations among Jewish and Non–Jewish patients," *Am. J. Hum. Genet.* 55:34–41 (1994).

Kaul, et al., "Identification and expression of eight novel mutations among Non–Jewish patients with canavan disease," *Am. J. Hum. Genet.* 59:95–102 (1996).

Kim, et al., "Preparation of multivesicular liposomes," *Biochim. Biophys. Acta* 728:339–348 (1983).

(List continued on next page.)

*Primary Examiner*—Dave T. Nguyen
(74) *Attorney, Agent, or Firm*—Holland & Knight LLP

(57) ABSTRACT

A gene delivery system which. is both safe and results in long-term expression throughout the brain has been developed. A lipid-entrapped, polycation-condensed DNA (LPD) system has been developed for brain gene delivery, using an adeno-associated vial. ("AAV") vector in which the transcription unit is flanked by the 145 bp inverted terminal repeats (ITR) of the adeno-associated virus. This AAV plasmid is more effective than a non-ITR containing plasmid in vivo. The results show that the LPD-AAV plasmid complexes efficiently transduce neurons and that gene expression can persist for over 10 months in the brain. Furthermore, the intraventricular delivery method with systemic hyperosmolality results in global gene delivery. The examples show that expression of the human aspartoacyclase ("ASPA") gene in children with this metabolic disorder can be obtained over a period of many months to a year, with functional activity.

18 Claims, No Drawings

OTHER PUBLICATIONS

La Salle, et al., "An Adenovirus Vector for Gene Transfer into Neurons and Glia in the Brain," *Science* 259:988–990 (1993).

Laimins, et al., "Osmotic control of kdp operon expression in *Escherichia coli*," *Proc. Natl. Acad. Sci.* 78:464–468 (1981).

Lee, et al., "Recognition of liposomes by cells: in vitro binding and endocytosis mediated by specific lipid headgroups and surface charge density," *Biochim. Biophys. Acta.*, 1103:185–197 (1992).

Liu, et al., "Role of liposome size and RES blockade in controlling biodistribution and tumor uptake of GM1–containing liposomes," *Biochim. Biophys. Acta* 1104:95–101 (1992).

Lusky, et al., "Bovine papilloma virus contains an activator of gene expression at the distal end of the early transcription unit," *Mol. Cell Bio.* 3:1108–22 (1983).

Matalon, et al., "Canavan disease: from spongy degeneration to molecular analysis," *J Pediatr* 127:511–517 (1995).

Felgner, "Particulate systems and polymers for in vitro and in vivo delivery of polynucleotides," *Advanced Drug Delivery Reviews*, 5:163–187 (1990).

Fiers, et al., "Complete nucleotide sequence of SV40 DNA," *Nature* 273:113–120 (1978).

Frahm, et al., "Localized proton spectroscopy using stimulated echoes," *J Magn Reson* 72:502–508 (1987).

Gao, et al., "Potentiation of cationic liposome–mediated gene delivery by polycations," *Biochemistry* 35:1027–1036 (1996).

Greenaway, et al., "Human cytomegalovirus DNA: BamHI, EcoRI and PstI restriction endonuclease cleavage maps," *Gene* 18:355–360 (1982).

Hwang, et al., "Short echo time proton magnetic resonance spectroscopic imaging of macromolecule and metabolite signal intensities in the human brain," *Magn Res Med* 35:633–9 (1996).

Iwamoto, et al., "Liposome–mediated BDNF cDNA transfer in intact and injured rat brain, " *Neuroreport* 7:609–612 (1996).

Jellinger, et al., "Juvenile form of spongy degeneration of the CNS," *Acta Neuropath* 13:276–281 (1969).

Johnson & Lloyd–Jones, eds., *Drug Delivery Systems* (Chichester, England: Ellis Horwood Ltd., 1987.

Kaplitt, et al., "Preproenkephalin promoter yields region–specific and long–term expression in adult brain after direct in vivo gene transfer via a defective herpes simplex viral vector," *Proc. Natl. Acad. Sci USA* 19:8979–8983 (1994).

Michaelis, et al., "Absolute concentrations of metabolites in the adult human brain in vivo: quantification of localized proton MR spectra," *Radiology* 187:219–27 (1993).

Mulligan, et al., "Expression of a bacterial gene in mammalian cells," *Science* 209:1422–27 (1980).

Naldini, et al., "In vivo gene delivery and stable transduction of nondividing cells by a lentiviral vector," *Science* 272:263–267 (1996).

Novotny, et al., "In vivo measurement of phenylalanine in human brain by proton nuclear magnetic resonance spectroscopy," *Pediatr Res* 37:244–249 (1995).

Ordidge, et al., "Image–selected in Vivo spectroscopy (ISIS). A new technique for spatially selective NMR spectroscopy," *J Magn Reson* 66:283–294 (1986).

Osborne, et al., "Transcription control region within the protein–coding portion of adenovirus E1A genes," *Mol. Cell Bio.* 4:1293–1305 (1984).

Ozband, et al., "Prenatal detection of Canavan disease," *Lancet* 337:735–6 (1991).

Pai, et al., "Toxicity of N–acetylaspartylglutamate and its protection by NMDA and non–NMDA receptor antagonists," *Neurosci Lett* 126:49–51 (1991).

Petroff, et al., "Initial observations on effect of vigabatrin on in vivo 1H spectroscopic measurements of gamma–aminobutyric acid, glutamate, and glutamine in human brain," *Epilepsia* 36:457–464 (1995).

Provencher, "Estimation of metabolite concentrations from localized in vivo proton NMR spectra," *Magnetic Resonance in Medicine* 30:672–679 (1993).

Roessler, et al., "Direct plasmid mediated transfection of adult murine brain cells in vivo using cationic liposomes," *Neurosci Lett* 167:5–10 (1994).

Samulski, et al., "Helper–free stocks of recombinant adeno–associated viruses: normal integration does not reguire viral gene expression," *J. Virol.* 63:3822–8 (1989).

Southern, et al., "Transformation of mammalian cells to antibiotic resistance with a bacterial gene under control of the SV40 early region promoter," *J. Molec. Appl. Genet.* 1:327–41 (1982).

Sugden, et al., "A vector that replicates as a plasmid and can be efficiently selected in B–lymphoblasts transformed by Epstein–Barr virus," *Mol. Cell. Biol.* 5:410–413 (1985).

Tallan, "Studies on the distrubution of N–Acetyl–L–Aspartic Acid in the brain," *J Biol Chem* 224:41–48 (1957).

Thierry & Dritschilo, "Intracellular availability of unmodified, phosphorothioated and liposomally encapsulated oligodeoxynucleotides for antisense activity," *Nucl. Acids Res.*, 20:5691–5698 (1992).

Toft, et al., "Magnetic resonance imaging in juvenile Canavan disease," *Eur J Pediatr* 152:750–753 (1993).

Van Bogaert, et al., "Sur une idiotie familale avec degenerescence spongieuse dy nevraxe," *Acta Neurol Belg* 49:572–587 (1949).

Wang, et al., "Highly efficient delivery mediated by pH–sensitive immunoliposomes," *Biochem.* 28: 9508–9514 (1989).

* cited by examiner

DELIVERY SYSTEM FOR GENE THERAPY TO THE BRAIN

This U.S. national phase application claims the benefit of U.S. Provisional Application No. 60/045,236, filed Apr. 17, 1997 and U.S. Provisional Application No. 60/050,617, filed Jun. 24, 1997 under 35 U.S.C. § 119(e). This is a U.S. national phase application of PCT/US98/07559 filed on April 17, 1998.

BACKGROUND OF THE INVENTION

The present invention is generally in the area of gene therapy, and especially prolonged delivery to and expression of enzymes in the brain.

Safe and effective methods for gene delivery into CNS neurons is necessary for successful genetic therapy of neurogenetic disorders. A large number of both viral and non-viral systems have been used for gene transfer into neurons both in vitro and in vivo. The most efficient systems for gene transfer are vectors based on viruses, most notably Herpes Simplex Virus (HSV) (Geller et al. 1995, During et al. 1994), Adenovirus (Davidson et al. 1993; La Gal La Salle 1993), Adeno-associated Virus (AAV) (Kaplitt and During, 1995; During and Leone, 1996) and Lentiviruses (Naldini et al. 1996).

Each of these systems have specific advantages based on efficiency of transduction, packaging capability, neurotropism and stability of expression but all share problems with varying degrees of inflammatory responses, potential for recombination and/or helper virus contamination and replication competency. These issues of safety have precluded the use of any these systems for neuronal gene transfer in humans. Alternative, potentially safer approaches for brain gene delivery include the use of naked, plasmid DNA as well as liposome-DNA complexes (Ulrich et al., 1996; Gao and Huang, 1995). Plasmid DNA appears efficient for transducing muscle (Davis et al., 1993) and liver (following intraportal administration, Wolf, personal communication). However, direct injection of plasmid DNA into the brain is very inefficient. Liposome-DNA complexes are perhaps a little more efficient than naked DNA but compared to viral vectors remain inefficient. Moreover gene transfer is generally transient (Roessler and Davidson, 1994; Kozarsdy and Wilson, 1993).

The major limitations facing current gene therapy is the lack of transduction efficiency and the inherent toxicity and immunogenicity of the most commonly-used vectors. Synthetic supramolecular complexes may provide for safe and effective gene delivery vehicles which could be used in the clinic. The specific problems that gene transfer in the brain present will require both improvements in the. vector system as well as delivery methods for global gene transfer.

A major limitation with brain gene transfer relates not only to the inefficiency of transduction of post-mitotic neurons and glia but also the inaccessibility of the brain. A problem facing neurological gene therapy is the need for global delivery and efficient transduction of cells throughout the brain for most neurogenetic disorders. Viral vectors do not diffuse well through brain parenchyma (Doran et al., 1995), perhaps reflecting size and affinity for cell membrane proteins. A variety of approaches have been used for global gene delivery. These include multiple stereotactic injections (Boviatsis et al., 1994); convection approaches (Oldfield et al., 1994) and hyperosmotic permeation of the blood-brain-barrier (bbb) (Neuwelt et al., 1994). Each of these methods is associated with significant morbidity, moreover the efficacy of each method is limited with bbb permeation effective for drug and gene deliver to tumors, which already have an impaired blood brain barrier, but very poor penetration into normal brain parenchyma.

It is therefore an object of the present invention to provide a means for improved delivery and expression of gene therapy, especially in the brain.

SUMMARY OF THE INVENTION

A gene delivery system which is both safe and results in long-term expression has been developed. The method yields widespread gene delivery throughout the brain. A lipid-entrapped, polycation-condensed DNA (LPD) system has been developed for brain gene delivery, using an adeno-associated viral ("AAV") vector in which the transcription unit is flanked by the 145 bp inverted terminal repeats (ITR) of the adeno-associated virus. This AAV plasmid is more effective than a non-ITR containing plasmid in vivo. In addition, an intraventricular delivery system has been developed to obtain widespread, global delivery.

The results show that the LPD-AAV plasmid complexes efficiently transduce neurons and that gene expression can persist for over 10 months in the rat brain. Furthermore, the intraventricular delivery method with systemic hyperosmolality results in global gene delivery. The examples show that expression of the human aspartoacyclase ("ASPA") gene can be obtained over a prolonged period of time. Trials in children with this metabolic disorder show that gene expression can be obtained over a period of many months to a year, with functional activity.

DETAILED DESCRIPTION OF THE INVENTION

A gene delivery system which is both safe and results in long-term expression has been developed. Furthermore, a method to obtain widespread gene delivery throughout the brain has been developed.

I. The Delivery System

Lipid Carriers

A lipid-entrapped, polycation-condensed DNA (LPD) system for brain gene delivery has been developed. The LPD particles are small, about 60–80 nm, monodispersed and colloidally stable (Gao and Huang, 1996). These particles have been shown in vitro to be highly effective in transduction efficiency (approximating that of adenoviral vectors) and safe (Huang, 1997).

The LPD complexes represent a significant step forward in non-viral, synthetic delivery systems:

1) The CD-Chol/DOPE liposome backbone is safe and has been used in 2 published clinical trials (Kaplen et al., 1995; Nabel et al., 1993) and 3 other ongoing protocols.
2) Both poly-L-lysine and protamine have been used clinically and appear safe with protamine being widely used as a heparin antagonist clinically.
3) AAV plasmids have previously been shown to enhance transduction efficiency and stability (Vieweg et al., 1995; Philip et al., 1994).
4) Both prolamine and poly-l-lysine have nuclear localization signals which may also improve transduction efficiencies.
5) Both protamine and poly-l-lysine efficiently complex plasmid DNA and result in condensation of the DNA. This condensed DNA changes from an external diameter of approximately 200nm to a 50–100 nm size when further complexed with the cationic liposome. These nano-LPD particles efficiently transduce post-mitotic cells including neurons and glia.

Other carriers such as liposomes, polycationic complexes and polymeric carriers can also be used, but are not preferred.

AAV Vectors

The gene to be delivered is placed into an adeno-associated viral vector. In the preferred embodiment, the transcription unit is flanked by the 145 bp inverted terminal repeats (ITR) of the adeno-associated virus. These ITRs have been shown to both enhance and prolong gene expression in both prostatic and lympocytic cell lines in vitro (Vieweg J, et al., 1995; Philip R, et al, 1994). The vector also includes a CMV promoter. This AAV plasmid is more effective than a non-ITR containing plasmid in vivo.

Other viral vectors can also be used, including retroviral vectors and adenoviral vectors, although these are not preferred for regulatory issues.

Means for Administration

In the preferred application for this technology, the viral vector is administered to the brain using a syringe or catheter. Intraventricular delivery is used to obtain widespread, global delivery.

Uptake is enhanced using agents such as mannitol, which cause a systemic hyperosmolality. For example, intraparenchymal penetration is enhanced by lowering brain interstitial pressure by the use of systemic mannitol (Rosenberg G A, et al., 1980).

II. EXAMPLES

The results show that the LPD-AAV plasmid complexes efficiently transduce neurons and that gene expression can persist for over 10 months in the rat and human brain. The intraventricular delivery method with systemic hyperosmolality results in global gene delivery. The LPD complexes also result in long-term expression and following intraventricular hyperosmolar administration can lead to global gene expression. LPD complexes provide for the excellent efficacy/toxicity ratio.

The examples show that expression of the human aspartoacyclase ("ASPA") gene can be obtained over a prolonged period of time. A deficiency in ASPA cause Canavan disease, or spongy degeneration of the brain. The human ASPA gene has been cloned, as described by Kaul, et al., *Genomics* 21(2), 364–370 (1994). Three point mutations predominantly found in Ashkenazi Jews cause the expressed enzyme to be completely inactive. Kaul, et al., *Am. J. Hum. Genet.* 55(1), 34–41 (1994). Other mutations have been found in non-Jewish patients. Kaul, et al., *Am. J. Hum. Genet.* 59(1), 95–102 (1996).

Children who are deficient in this enzyme quickly loose brain function, deteriorating to a vegetative state by a few years of age, and dying shortly thereafter. There is no treatment for these children.

Example 1

Construction of the AAV Vector

Materials and Methods

The recombinant DNA used for the study contained three general elements. The plasmid backbone is derived from pEMBL and is a high copy *E. coli* based plasmid with an ampicillin resistance gene and an *E. Coli* origin of replication. The plasmid contains 145 base terminal repeats from the human non-pathogenic, parvovirus adeno-associated virus (AAV) (Kaplitt and During, 1995). These sequences are non-coding and form a hairpin secondary structure which is important for both transduction efficiency of the plasmid as well as stability of expression of the flanked transcription unit (Philip et al., 1994; Viewig et al., 1995). The third component of the plasmid which is spanned by the AAV terminal repeats is the transcription unit consisting of the CMV promoter (650 bases), and either the *E. Coli* lacZ gene (encoding the marker protein, β-galactosidase, AAVlac) or the full-length human ASPA cDNA (1.4 kb, obtained from Drs. Kaul and Matalon of Miami Children's Hospital, pAAVaspa) and the SV40 early polyadenylation signal (400 bases).

Regulatory Elements:

The promoter is the 650 base pair early cytomegalus virus (CMV) promoter which was obtained from the commercial (Invitrogen, Inc.) plasmid pcDNA1. This promoter is a very strong constitutive promoter active in all eukaryotic cell types. There has been some variable loss of expression associated with the use of this promoter in studies of gene transfer which may reflect methylation. However, this promoter has been widely used in clinical gene transfer experiments. No loss of expression over time has been observed in lentiviral vectors in the brain (Naldini et al., 1996) and AAV vectors in muscle (Xiao et al., 1996). The polyadenylation signal was the XV40 polyA derived from the Invitrogen plasmid pREP4.

Steps Used to Derive the DNA Construct:

Plasmid pSub201 (Samulski et al., 1989) was digested with XbaI to remove nearly the entire AAV genome, leaving only the terminal repeats. A CMV promoter-lacZ gene—SV40 polyA signal cassette was isolated from plasmid pHCL (Kaplitt et al., 1994) by digestion with SpeI and XbaI, and this was inserted into XbaI-digested pSub201 to create pAAVlac. A second plasmid was created (pAAV-CMV-polyA) by digestion of pAAVlac with HindIII and XbaI to remove the lacZ gene and polyA signal, followed by insertion of a HindIII-XbaI fragment from pREP4 (Invitrogen), containing a polylinker and SV40 polyA signal. This plasmid was digested with NheI and NotI, followed by insertion of a human ASPA cDNA released from the plasmid pGCMV-ASPA (Kaul et al., 1993) by a XbaI—NotI digestion. The sequence of the final construct was confirmed by automatic sequencing on an ABI Model 377 sequencer. The plasmid was made under sterile conditions in the presence of ampicillin using the *E. Coli* strain DH5α and purified in facilities at the University of Pittsburgh.

Example 2

Delivery to and Expression in Animals of β-galactasidase

Materials and Methods

Liposomes and Polycations

The liposome was made under sterile, good manufacturing processing ("GMP") conditions. The liposome is a mixture of the neutral lipid DOPE (dioleoyl phosphatidylethanolamine) with a cationic liposome, DC-Chol (3b-[N-(N',N'dimethylaminoethane) carbamoyl] cholesterol). The polycations used included poly-L-lysine (18,900 m.w., Sigma, St. Louis) and protamine sulfate (USP grade, Eli Lilly).

Evaluation of Gene Expression

X-gal Histochemistry

Animals were deeply anesthetized and transcardially perfused with PBS followed by 2% paraformaldehyde with 5 mM EGTA. This fixation method completely eliminates staining due to endogenous enzymes (Kaplitt et al., 1991; Kaplitt et al., 1994). Brain sections were stained with the histochemical substrate X-gal as previously described (During et al., 1994; Kaplitt et al., 1994).

NF. GFAP and B-galactosidase Immunocytochemistry

For immunocytochemical (ICC) analysis of brain sections, rats were deeply anesthetized with chloral hydrate and perfused with 1 M PBS (ph 7.3) followed by 4% paraformnaldehyde (PF). Brains were removed and post-fixed (3–4 hours) in 4% PF followed by ascending sucrose solutions (10/15/30% in PBS). Sections (7–30 $\mu$m) were cut in a cyrostat (Reichert-Jung) and mounted on polylysine-coated slides. Sections were initially incubated in blocking buffer (5% goat serum (GS)/5 % normal horse serum (NHS) in 1 M phosphate buffered saline (PBS)), followed by 2–4 hours incubation at room temperature with mouse Ig antibody.

Intracerebral Gene Delivery

Groups of rats were maintained in a housing facility at the University of Auckland School of Medicine under controlled lighting (12 hour day/light cycle), temperature and humidity with ad libitum access to food. The animal protocol was approved by the Yale Animal Care and Use Committee and the University of Auckland Animal Ethics Committee. All surgeries were carried out under general anesthesia using ketamine/xylazine (70/7 mg $kg^{-1}$) administered intraperitoneally. A stereotactic frame (Kopf) was used for all surgeries:

Intraparenchymal injections were made into the hippocampus (A-P=−2.9; M-L=1.6; D-V=2.0), striatum (A-P=0.6; M-L=2.4; D-V=5.0) or intracerebroventriculariy A-P=0.9; M-L=1.5; D-V=3.2).

The following groups of animals were studied:

1) Intraparenchymal LPD (poly-L-lysine)
2) Intraparenchymal lipofectamine
3) Intraparenchymal LPD (protamine)
4) Intraparenchymal LPD (plasmid without AAV ITR)
5) Intraventricular LPD (poly-L-lysine)
6) Intraventricular LPD (protamine)
7) Intraventricular LPD (protamine plus systemic mannitol)
8) Intraventricular LPD (AAVaspa; poly-L-lysine with systemic mannitol)
9) Repeated dosing of LPD Results Intraparenchymal delivery of an AAV expression plasmid together with lipofectamine resulted in limited expression surrounding the needle-tract with little penetration into the tissue. Furthermore, expression diminished over time although a few positive cells were apparent at one month following surgery. In comparison, the delivery of the same plasmid following condensation with poly-L-lysine and complexing the CD-Chol/DOPE resulted in a marked increase in expression extending to one month. The use of protamine instead of poly-L-lysine resulted in a further enhancement of expression at both 1 week and one month. With a volume of 2–4 microliters which resulted in local needle tract expression with lipofectamine, more widespread expression was obtained with the LPD complex. Furthermore, if the injection volume was increased to 8 microliters much wider expression was obtained with preferential spread of the complex and gene expression along white matter tracts and blood vessels.

The use of the AAV ITR-containing plasmids resulted in similar expression at 1 week but greater expression at one month and 8 months when compared to the LPD complex using the identical expression cassette not flanked with the ITRs.

Intraventricular administration of the LPD complexes resulted in expression in periventricular cells extending into parenchyma. The parenchymal spread was enhanced by the use of systemic mannitol which drops interstitial pressure and increases CSF flow away from the ventricles.

In the rat, the LPD/AAVlac complex has been injected into both brain parenchyma as well as intraventricularly. Results have shown that in the first week (Days 3 to 7) following the injection of 2 to 6 microliters of the complex at a concentration of 300 $\mu$g DNA per ml of LPD, $10^3$ cells are transduced down the needle track and in the vicinity of the LPD diffusion (the LPD/plasmid complex) which follows white matter tracks within the brain and tracks along planes between brain regions and groups of cell nuclei. At two and six months, $10^2$–$10^3$ remain readily detectably with X-gal staining, suggesting minimal loss of expression over this time period.

Example 3

Expression of Functional ASPA in Human Cells

In vitro studies used the 293 human embryonic kidney cell line. As there is not an ASPA antibody suitable for immnunocytochemical or immunoblot analysis, both in vitro and in vivo efficacy were initially assessed using LPD with a marker gene (*E. coli* lacZ plasmid expressing β-galactosidase).

In vitro efficacy is dependent on the relative concentrations of DNA, liposome and plasmid and under optimal concentration efficiencies of 80% are obtained. In vivo efficacy using injection volumes of 2–50 microliters (at a DNA concentration of 300 $\mu$g/ml of LPD) demonstrate transduction of $10^3$–$10^5$ cells.

Cultured cell results show mean levels of ASPA enzyme activity of 0.40±0.12 mU/mg protein following LPD/ASPA transduction of 293 human embryonic kidney cells with an approximate 5 % transduction efficacy. This compares to activity of 1.04±0.04 mU/mg protein in rat cortex. If one percent of enzyme activity is sufficient to influence disease progression, then one would aim for a transduction efficiency of approximately 0.1 % in defined (periventricular) regions.

Example 4

Safety and Efficacy Studies in Rats

The same techniques described in example 2 were used to administer the vector of example 1 to rats and to monkeys.

Expression out to 10.5 months using the LPD/AAVaspa construct following intraventricular administration has been observed. As there is no antibody to ASPA suitable for immunohistochemical analysis, one can not distinguish at the protein level the transgene-encoded ASPA from the wild enzyme. RT-PCR was therefore used to follow ASPA transgene expression. Widespread expression was obtained throughout the brain, extending to 10.5 months following intraventricular administration. This !20 supports the expression data on B-galactosidase expression following intraventricular of LPD/AAVlac. Using an intraventricular approach together with systemic mannitol to reduce interstitial pressure, widespread expression extending several millimeters from the ventricular surface was observed.

Although the number of transduced cells as a percentage of total brain cells (target cells) is low, it can reach 106 cells following high volume (10 –20 microliters) intraventricular injection. From the in vitro work, it is known that relatively low transduction efficiencies can lead to wild-type levels of the enzyme and that the protein is functionally active.

Neurosurgical stereotactic injections were performed on a total of 400 rats with either the AAVaspa or AAVlac plasmid, DC-Chol/DOPE and protamine (LPD) complex and PBS-treated controls without any toxicity or adverse effects on rat behavior, feeling or general health. All these rats were weighed on a twice weekly basis and were observed for coat quality (grooming behavior) and conjunctivitis (probably the most sensitive indicator of general stress) as well as feeding and drinking behavior. A summary of animal studies follow:

| Experimental Animals and # | Route of Administration | Volume | Duration of Study | Gene | Outcome |
|---|---|---|---|---|---|
| Rats, n = 3 × 60 groups (4 volumes by 5 timepoints by 3 treatments) | i.c.v. | 5, 10, 20, 50 μl | 7 days, 1, 3, 6 and 9 months | LacZ or ASPA or PBS | No toxicity |
| Rats, n = 3 × 60 groups (4 volumes and 5 timepoints) | i.p | 2, 5, 8, 12 μl | 3, 7 days; 2, 6, 8 months | LacZ or ASPA or PBS | No toxicity |
| Rats, n = 5 × 3 treatment groups | i.c.v. repeated dose at 1 month | 50 μl | 3 months | LacZ or ASPA or PBS | No toxicity |
| Rats, n = 5 × 3 treatment groups | i.p. repeated dose at month | 112 μlμl | 3 months | LacZ or ASPA or PBS | No toxicity |
| Rats, n = 2 for 6 groups (2 doses and 3 treatments) | i.c.v. very high dose | 100, 250 μl | 2 weeks | LacZ or ASPA or PBS | Well tolerated* |

i.c.v. = intracerebroventricular
i.p. = intraparenchymal

All rats in this high dose group (including control rats injected with the reporter gene and sterile Phosphate Buffer Saline) displayed sleepiness and hypomotility (measured by the open-field test and grooming behavior) during the 24 hours following the surgery. Rectal temperature raised up by 2° C. in all animals for 10 hours post-surgery. The feeding rate, which decreased mildly post surgery in all animals, went back to baseline after 48 hours.

An additional subset of five animals were infused with AAVaspa/LPD (50 microliters) via an indwelling ventricular cannula. These animals were followed with daily weights, temperature and behavioral tests. The animals were followed with rectal temperatures both in the morning and evening.

Behavioral analysis included:

1) Open filed behavior and locomotion;

2) Spatial navigation behavior using the Banes circular platform;

3) Response to novel environment;

4) Rigidity/catatonia testing;

5) Motor coordination and climbing using the inclined beam test;

No adverse effects were noted over a one month period. Histological analysis following sacrifice. Animals were euthanized and brains perfused with paraformaldehyde. Brains were sections at 30 micron thickness. Sections were stained with H&E and underwent microscopic evaluation. No inflammatory responses/neuronal injury.

Although light microscopy evaluation of H&E stained tissue did not reveal any inflammatory cell infiltrate into the brain and normal neuronal and glial morphology with complete integrity of the tissue, a recent study by Byrnes et al. (1995) has shown that adenoviral vectors result in inflammation and increased expression of immunological markers including MHC Class I expression and T cell infiltration. A group of 6 rats were therefore injected with the AAVaspa/LPD complex intraventricularly (20 μl) and a group of 6 rates intraparenchymally (8 μl) to determine whether the LPD complex resulted in T cell infiltration and a change in MHC expression. A control, saline (PBS) treated group of 6 animals was used as a control for both groups. Animals were sacrificed at 4 days and 1 month with brains perfused and fixed. Forty micron coronal sections were cut on a cryostat and the primary antibodies OX-18 (purified antibody which reacts with a non-polymorphic determinant of rat MHC class I antigen) and OX-35 (reacts specifically with the CD4 antigen on T helper cells, thymocytes, and activated macrophages and microglia) were applied (both obtained from Pharmacia). In none of the intraventricular-treated animals were CD4-IR cells identified nor was there any neuronal MHC Class I expression. In the intraparenchymally-injected animals which were sacrificed at 4 days, a small number of CD4iIR cells as well as OX-18 staining was present in the immediate vicinity of the needle tract, however this increase was noted in both PBS and LPD-injected animals. At one month, there was no intraparenchymal staining with either OX-18 or OX-35 in either group of animals. Although studies did not include an adenoviral vector-treated group, in comparison with the data presented by Charlton for adenovirus (Byrnes et al., 1995) and HSV (Wood et al., 1994) in. which the vectors resulted in severe widespread expression of MHCI antigents, or LPD and PBS-treated animals had significantly less staining of these markers with only moderate staining immediately around the injection site at 4 days with OX-18 and few CD4 positive cells with complete resolution of the inflammation at one month. Moreover, the intraventricular injection did not result in any parenchymal inflammation. Together with the persistent expression at 10 months (in contrast to adenoviral vectors with marked loss of expression over 1–3 months), this data suggests that the LPD complexes are significantly less immunogenic than current generation viral vectors.

PCR analysis of testes was carried out in 10 LPD-treated rats and a group of 15 cynomologous monkeys treated with other vectors (intraparenchymal and intraventricular injections of recombinant AAV and AAV plasmids with poly-L-lysine/liposome complexes). Foreign DNA was not detected in the gonads. In addition, a PCR signal was not detected in other non-CNS tissues including liver, spleen and kidney.

Example 5

Expression in Initial Human Clinical Trials

Approval for a Phase I clinical protocol was obtained from the following committees: Yale University School of Medicine Human Investigation Committee; North Health (Auckland Hospital, New Zealand) Ethics Committee; University of Auckland Ethics Committee Biosafety Committee (Auckland Hospital); and New Zealand Gene Technology Advisory Committee.

Two children (L.K. aged 19 months and A.M. aged 24 months) were enrolled in the initial Phase I trial using the LPD/ASPA complex.

Clinical Report Summary at 6 Months

The surgical procedure was uncomplicated apart from a mild, transient post-operative fever (<40° C.) in both children lasting for less than 72 hours. One child (A.M.) had some minor pulsatility over the burrhole site associated with facial dependent oedema which settled over 72–96 hours with complete resolute of the presumed dural CSF leak. CT Scans post surgery were completely normal. Both children were drowsy for the first 24–48 hours post-surgery but by 3 days were as alert (or more so) than baseline. Blood tests, both hematological and biochemical, remained within the normal range. Both children were discharged at one week following surgery. Findings are reported for evaluations prior to surgery and 1, 2, 4 and 6 months postoperatively.

Prior to surgery, L.K. was evaluated using the Gesell-Provence Developmental Schedules (GPDS), a neurodevelopmental instrument that provides a developmental age equivalent based on a profile of functioning across five domains—gross and the fine motor, adaptive or problem solving, language and social development. The severity of L.K.'s developmental delays precluded an accurate age equivalent or developmental quotient as she demonstrated considerable variation in her performance across developmental domains and a basal performance level could not be obtained. However with this caveat in mind, her highest level of functioning was less than a 12 week age equivalent and in some areas less than an 8 week equivalent. Notably L.K. needed complete head support, arched her back in extension when moved, did not reach for objects, and had minimal grasp and extremely limited visual tracking. At one month post surgery, L.K. was re-evaluated by the same observer. The most notable difference was overall greater awareness and alertness. She was more responsive and smiled more and often spontaneously. She also initiated social interaction on her own. Facial expressions were brighter and more differentiated. She was able to chew and swallow solid foods in a coordinated fashion. She was able to hold her head unsupported for a few seconds and was able to turn from her side to her back and bear some weight on her legs. L.K. also had notable gains in language and social skills. She was beginning to make a number of differentiated vocalizations including consonant sounds. She responded to simple statements like "I want a drink" by opening her mouth and used an open mouth to indicate "more". Her vocalizations appeared to indicate different needs and she appeared to understand and respond to a number of phrases (by head turning, smiling, visual regard). Her development age equivalent appeared to be at 3 months. At six months following surgery, further skills were achieved. K.K. was able to hold her head up unsupported for up to 8 minutes. She was able to grasp objects, and was much clearer in expressing her wants and displeasure.

A.M. was evaluated at age 19 months (5 months prior to surgery) using the GPDS, at which time she had notable head lag and was unable to hold her head unsupported. She was not reaching for objects but was able to hold an object briefly if placed in her hands. She appeared interested in novelty and turned to sound. She laughed and cooed but made no consonant sounds. Her developmental age was between 12–16 weeks. At reassessment immediately prior to surgery, A.M. had lost a number of developmental skills including less responsivity to environmental stimuli, poorer head control and much increased muscle tone with marked overall rigidity. Her baseline developmental age equivalent immediately presurgery had deteriorated to less than 12 weeks. At one month following surgery, A.M. was more interested in and aware of her surroundings, had more differentiated facial expressions, had better visual tracking and was making eye contact when spoken to. She was turning to look and moved her head back and forth. She also had less drooling, more coordinated swallowing and regular bowel motions. A.M. was significantly less rigid with more spontaneous and purposeful movement. She was able to put her arms around her parents neck when held, and also showed some motor activity in the midline evidenced by her grasping hands together on several occasions. Her developmental age equivalent at that time was approximately between 12–16 weeks. At 2 months post surgery, A.M. had maintained her developmental state with some minor advances. Specifically she showed greater interest and awareness of her surroundings, more differentiated facial affect and greater social interactiveness. She was also better at chewing and swallowing. However, her neurological state subsequently plateaued with no significant changes between 2 and 6 months post surgery.

In addition to developmental and neurological assessment, both children underwent repeated visual evoked potentials (VEDPs) and proton spectroscopy of regional brain NAA. L.K. is baseline VEP to pattern reversal was performed binocularly, since she would not tolerate monocular testing. There was significant bilateral delay with the P100 (Positive wave observed in normals at 100 ms) latency to 154.4 ms. Moreover the amplitude from P1 to N2 was 0.83 uV (Normal>1.5 uV). This test suggested bilateral optic pathway pathology. On retesting at 2 months post surgery, VEPs were normal with latency of 85.8 ms and amplitude of 2.39 uV in both eyes. At 5 months post surgery, VEPs remained within the normal range. L.K. was also assessed by an ophthalmic surgeon in view of hyperopia and astigmatism. Prior to surgery, significant deterioration had occurred with loss of fixation, amblyopia, exotropia, horizontal and occlusion nystagmus. On re-evaluation, 2 months post surgery, L.K. showed good fixation, no signs of amblyopia, partial resolution of exotropia and the nystagmus had completely resolved. A.M. was unable to cooperate sufficiently to obtain interpretable VEPs both prior to, and following surgery.

Baseline NMRS was performed at Yale, however a system upgrade required that postoperative NMRS was conducted at Childrens' Hospital in Philadelphia (CHOP) and an additional control group of 5 Canavan children (untreated and ages 6–30 months) was also studied at CHOP.

L.K.'s NAA baseline concentration was quantiated at 15.4 mM in the occipital region. Parietal and frontal lobe concentrations were also significantly above control values despite an occipito-frontal gradient with lower values anteriorly on proton spectroscopic imaging. Mean concentration and standard deviation (S.D.) of NAA from 8 control spectra (in 8 subjects) measured from frontal, parietal and occipital lobe is 9.8+0.6 mM (no significant regional differences). At one month post surgery, occipital region remained elevated above normal at 14.5 mM, however both parietal and frontal lobes were now within the low normal range, NAA=9.4 and 8.4 mM respectively. At 4 months the occipital, parietal and frontal NAA concentrations were 16.2, 10.0 and 9.1 mM respectively. Therefore normal levels of NAA were maintained in both parietal and frontal regions with high levels persistent in the occipital lobe.

A.M.'s baseline NAA concentration was 15.6 mM in occipital lobe. At one month NMRS at CHOP of occipital, parietal and frontal regions showed concentrations of NAA of 12.8, 10.0, 9.6 mM. At 4 months, levels were 12.7, 12.6 and 12.9 mM respectively.

Untreated Canavan children scanned at CHOP using the same magnet and parameters gave mean +S.D. values of 15.7+1.5, 13.9+2.0, 13.6+1.8 mM for occipital, parietal and frontal lobes respectively.

These NMRS results show normal concentrations of NAA in both frontal and parietal regions for both children at one month, with maintenance of normal values in these regions at 4 months for L.K., but a reversion to the Canavan range at this timepoint for A.M., although A.M.'s occipital NAA concentration of 12.7 mM remain lower than all other Canavan children (range 14.7 –18.0 mM).

Clinical Report Summary at 12 Months Report on L.K.

Biochemical

Mean concentration and standard deviation (S.D.) of NAA from 8 control spectra (in 8 subjects) measured from frontal, parietal and occipital lobe was 9.8+0.6 mM (no significant regional differences). L.K.'s baseline NAA levels (carried out at Yale) was elevated in all brain regions (15.4 mM in occipital cortex with a posterior-anterior gradient, but frontal lobe levels markedly elevated above control values). At one month post surgery, occipital region NAA remained elevated above normal at 14.5 mM, however both parietal and frontal lobes were within the low normal range, NAA=9.4 and 8.4 mM respectively.

At 4 months the occipital, parietal and frontal NAA concentrations were 16.2, 10.0, and 9.1 mM respectively and at 9 months were 16.5, 10.2 and 10.4 mM respectively. A proton NMRS spectroscopy scan was conducted at 12 months following surgery in late February, 1997. The report shows that her NAA levels in the occipital lobe was 16.9 mM, parietal lobe 10.4 mM and the frontal cortex 9.8 mM. These values are essentially unchanged from the values obtained at 9 months and both frontal and parietal lobes remain within the normal range for age-matched children.

MRI

Serial MRI studies of the brain were performed using a 1.5 tesla magnet conducted at the same time as the proton NMRS. Unenhanced T1-weighted images were acquired in the sagittal and transverse planes. The baseline study (within 3 weeks of surgery) showed diffuse, abnormal prolongation of the T1 signal within the subcortical and deep white matter. These multiplanar images with increased T1 relaxation time in white matter are consistent with the spongiform degeneration of oligodendrocytes characteristic of Canavan Disease. At four months post surgery a repeat examination was performed and compared with the previous study. Again, diffuse, abnormal prolongation of the T1 signal within the subcortical and deep white matter was demonstrated which was unchanged from the initial study. At 9 months, the T1-weighted sequences showed less pronounced hypointensity than the previous studies. In particular, the subcortical white matter showed a decrease in the abnormal prolongation of the T1 signal. At 12 months post surgery, a myelin quantitation MRI study was repeated using sagittal T1-weighted, axial T1 and T2, axial FLAIR and coronal T2. The exam was compared to previous studies. At this time, it was noted that there has been definite interval myelination. Specifically, there was evidence of improved (although not normal) myelination of the corpus callosum as well as the basal ganglia and the posterior limb of the internal capsule. The myelination pattern at this latest time is roughly what would be expected in a 4 month old infant. The myelination in the baseline and 3 month studies was more suggestive of a pattern expected nearer birth. This evaluation and interpretation was conducted by Dr. Larissa Bilianuk, M.D. and Dr. Robert Zimmerman, board certified neuroradiologists at Childrens Hospital of Philadelphia. These changes in the MRI are suggestive of a more developed myelin pattern i.e., remyelination and/or reduced spongiform degeneration of the oligodendrocytes. In addition, the latest proton NRMS data suggests that some level of transgene expression has persisted out to 12 months in L.K. Furthermore, the MRI data suggesting new myelin formation is dramatic, however it is consistent with, and perhaps to be expected, in light of the observed gain in neurological function (being able to hold her head up) and normalization of visual evoked potentials. Moreover, the timing of reaching the visible threshold for detecting a change in the abnormal T1 relaxation time is consistent with our estimates for new myelin formation following biochemical normalization.

Neuro-ophthalmic Evaluation

In the months prior to surgery, significant deterioration had occurred with loss of fixation, amblyopia, exotropia, horizontal and occlusion nystagmus. On re-evaluation, 2 months, 6 months, 9 months and again at 12 months post surgery, L.K. showed good fixation, no signs of amblyopia, partial resolution of exotropia and the nystagmus had completely resolved.

Visual Evoked Potentials

The visual evoked potentials had markedly delayed latency and reduced amplitude prior to the surgical intervention. On repeat testing at 2 months post surgery, the VEPs lay within the normal range. At the most recent assessment (Mar. 12, 1997) VEPs as well as AEPs (auditory evoked potentials) were normal.

Neurodevelopmental Assessment

Neurodevelopmental assessments have shown continual further improvements in L.K. She has been re-evaluated at 12 months post surgery (chronological age 33 months) and her functional level in scattered skill development in specific areas of cognition, expressive language and social emotion is the equivalent of a normal 18 to 24 months age child. L.K.'s speech therapist has determined that she is able to understand and responds appropriately and selectively to simple commands in English and Spanish (her nanny's native language is Spanish). There were other the very evident improvements in L.K.'s neurological state. She was far more interactive with improved visual regard and motor function reaching out with both hands, in addition to holding her head up for extended periods.

Report on A.M.

Biochemical

Proton MR spectroscopy examinations were performed on Magneto S using single vowel STEAM. At one month post surgery, MRS at CHOP of occipital, parietal and frontal regions showed concentrations of NA of 16.6 mM, 10.1 mM and 9.9 respectively. At 4 months post surgery, levels were 11.6 mM, 11.5 mM and 12 mM respectively. At 6 months post surgery, levels were 11.7 mM, 11.7 mM and 11.8 mM. At 9 months post surgery, levels were 12.7 mM, 13.8 mM and 12.5 mM. At one month, both parietal and frontal lobe NA levels were within the normal range. However, by 4 months these values were elevated and have remained elevated since. Only A.M's occipital NA concentration of 12.7 mM remains lower than the Canavan range. Indeed untreated Canavan children scanned at CHOP using the same magnet and parameters gave mean +S.D. values of 15.7+1.5, 13.9+2.0, 13.6+1.8 mM for occipital, parietal and frontal lobes respectively.

MRI

A.M.'s MRI of the brain was performed with the same magnet and same parameters of L.K. as MRI. The 9 month MRI report demonstrates diffuse prolongation of the T1 and T2 signal in the cerebellar and cerebral white matter. This is slightly more marked around the atria and occipital horns of the lateral ventricles. Abnormal signal is seen within the globus pallidi as well as the thalami. There is abnormal signal within the discending tracts of the brainstem, including dorsal midbrain and pons as well as the cerebral peduncles. There is dilatation of the atria and occipital horns of the lateral ventricles, likely on the basis of ex vacuo change. No deterioration had been noticed since surgery, but unlike L.K. there was no significant changes in the white matter signal. A.M.'s 12 month follow-up MRI report shows no interval remyelination.

Neurological Examination

A.M. was increasingly rigid prior to surgery showing evidence of neurological deterioration. Following gene transfer, she was re-evaluated at one month. Significant improvements were noted in A.M. and she was assessed as a 12–16 week age equivalent (8–12 week prior to surgery). At six months, there was a plateauing in the clinical state of A.M. but she remained at a higher level of neurological function than that prior to surgery. The improvement in neurological and developmental state was consistent with the transient normalization of brain NA in defined brain regions. A.M. had smaller and relatively short-lived changes than L.K. with respect to NA perhaps reflecting a transient CSF leak following surgery and is likely therefore to have had less CNS gene transfer. This is also consistent with a lesser clinical improvement than that observed with L.K. No significant changes have been determined in her 12 month follow-up examination, with her clinical state essentially stable over the last 9 months.

Neuropthalmic Evaluation

Over the 12 month period following surgery there have been no signs of amblyopia, exotropia or nystagmus.

Visual Evoked Potentials

A.M. was unable to cooperate sufficiently to obtain interpretable VEPs both prior to, and following surgery at 3 months. At 12 months, A.M. was able to cooperate sufficiently. At this time her pattern reversal VEP shows a bifid cortical potential which was reproducibly demonstrated. This bifid response may represent an abnormality, although the latencies of the second negative and positive deflections are within the normal range. The significance of the bifid pattern can not be resolved in a child of this age and would require lower field stimulation alone.

Neurodevelopmental Assessment

A.M. current developmental age equivalent in all areas of functioning is 12–16 weeks (compared to 8–12 weeks). However, she showed some notable changes since the gene therapy procedure which stabilized at 6 months post-surgery. The changes include an increase in her interest and awareness of her surroundings, more eye contact with visual tracking, more differentiated facial expression, greater social interactiveness and more coordinated bowel function and swallowing with less drooling. No further improvements have been noticed since the neurological assessment at 6 months post-surgery. In summary A.M.'s improvements have not been as marked as in L.K., although she also has maintained her improvement with some slight gains, for example, she rolled over and fell out of bed last month. Although this sounds trite, Canavan children do not fall out of bed, they are virtually immobile, mostly rigid with very few spontaneous movements and unable to roll over. The improved motor function in A.M. is also matched by improved responsiveness, although her level of functioning is not as high as L.K.

Clinical Outcome Summary

At twelve months following surgery, both children are at a higher level of neurological function than that prior to surgery. This study as a Phase I trial with only 2 children was not designed for and does not have statistical power to assess clinical efficacy. Importantly however, it does demonstrate safety and tolerability in these two children with no significant adverse effects and only a transient postoperative fever. The improvement in neurological and developmental state is consistent with a normalization of brain NA in defined brain regions. Moreover, A.M. had smaller and more transient changes with respect to NA perhaps reflecting the transient CSF leak following surgery and is likely therefore to have had less CNS gene transfer. This is also consistent with a lesser clinical improvement than that observed with L.K. Although lowering of CSF pressure may result in transient benefit in Canavan children with raised intracranial pressure (personal communication, S. Gluckman), both children studied in this trial had normal opening CSF pressures, the timecourse of improvement is inconsistent with a temporary CSF tap, and the one child with a transient CSF leak showed less improvement. In summary, intraventricular delivery of LPD complexes in these 2 children was safe and well tolerated. MRS, VEPs and neurodevelopmental assessment suggest that gene transfer occurred. Analysis of white matter signal in the repeated MRI is strongly suggestive of remyelination in one child.

Example 6

Additional Human Clinical Trials

Nine additional children have been treated using the same methodology (10 mls, same vector, administered intracerebral ventrically). The data show safety and efficacy, as measured by neurological improvements and normalization of evoked potentials.

The following abbreviations were used herein: NGF—nerve growth factor; BDNF—brain derived neurotrophic factor; GDNF—glial cell line-derived neurotrophic factor; GABA—gamma-amino butyric acid; CNS—central nervous system; AAV—adeno-associated vector; ITR—inverted terminal repeats; LPD—lipid-entrapped, polycation-condensed DNA; bbb—blood-brain-barrier; CMV—cytomegalovirus; ASPA—aspartoacyclase; GMP—guanosine monophosphate; DOPE—dioleoyl phosphatidylethanolamine; DC-Chol—3b-[N-(N', N'dimethylaminoethane)carbamoyl]cholesterol; EGTA—ethylene glycol-bis(β-aminoethyl ether); ICC—immunocytochemical; PF—paraformnaldehyde; GS—goat serum; NHS—normal horse serum; PBS—phosphate buffered saline; CSF—cerebral spinal fluid; NF—necrosis factor/nuclear factor/nerve factor/neurofibromatosis; GFAP—glial fibrillary acidic protein; NAA—N-acetylaspartate; H&E—hemotoxylin & eosin; MHC—major histocompatibility compex; HSV—herpes simplex virus; GPDS—Gesell-Provence Developmental Schedules; VEP—visual evoked potentials; CHOP—Childrens' Hospital of Philadelphia; NMRS—nuclear magnetic resonance scan; AEP—auditory evoked potentials.

The teachings of the references cited herein are specifically incorporated by reference.

We claim:

1. A method for increasing gene expression in cells of the central nervous system comprising administering at or adjacent to cells of the central nervous system tissue, cation lipid associated polycation-condensed nucleic acid, wherein the cation lipid associated polycation-condensed nucleic acid comprises a cationic lipid, a polycation, and a nucleic acid encoding a protein associated with a genetic disorder, wherein the cation lipid associated polycation condensed nucleic acid enhances gene expression in the cells of the central nervous system, wherein the nucleic acid does not include an AAV coding sequence.

2. The method of claim 1 wherein the cation lipid associated polycation condensed nucleic acid comprises dioleoyl phosphatidylethanolamine.

3. The method of claim 2 wherein the cationic lipid is 3b-[N-(N',N'dimethylaminoethane) carbamoyl]cholesterol.

4. The method of claim 1 wherein the polycations are selected from the group consisting of polylysine and protamine sulfate.

5. The method of claim 1 wherein the nucleic acid comprises an early cytomegalo virus promoter, a polynucleotide sequence coding for a protein associated wit a neurogenic disorder, and an SV40 poly A signal.

6. The method of claim 5 wherein the polynucleotide sequence comprises a nucleic acid sequence encoding ASPA.

7. The method of claim 1 wherein the central nervous system tissue is brain tissue.

8. The method of claim 7 wherein the cation lipid associated polycation-condensed nucleic acid is administered intracerebrally.

9. The method of claim 4 wherein the lipid-entrapped polycation-condensed nucleic acid is administered intraparenchymally or intraventricularly.

10. A composition for increasing gene expression in cells of the central nervous system comprising cation lipid associated polycation-condensed nucleic acid, wherein the cation lipid associated polycation condensed nucleic acid comprises a cationic lipid, a polycation, and a nucleic acid encoding a protein associated with a neurogenetic disorder, wherein the cation lipid associated polycation condensed nucleic acid enhances gene expression in the cells of the central nervous system, wherein the nucleic acid does not include an AAV coding sequence.

11. The composition of claim 10 wherein the polycations are selected from the group consisting of polylysine and protamine sulfate.

12. The composition of claim 10 wherein the cation lipid associated polycation condensed nucleic acid comprise dioleoyl phosphatidylethanolamine.

13. The composition of claim 12 wherein the cationic lipid is 3b- {N-(N',N'dimethylaminoethane) carbamoyl} cholesterol.

14. The composition of claim 10 wherein the nucleic acid to be delivered comprises adeno-associated virus inverted terminal repeats flanking an expression sequence.

15. The composition of claim 10 wherein the nucleic acid comprises an early cytomegalo virus promoter, a polynucleotide sequence coding for a protein associated wit a neurogenic disorder, and an SV40 poly A signal.

16. The composition of claim 15 wherein the polynucleotide sequence comprises a nucleic acid sequence encoding ASPA.

17. The composition of claim 10 wherein the nucleic acid comprises a nucleic acid sequence encoding ASPA.

18. The method of claim 1 wherein the administration of the cation lipid associated polycation-condensed nucleic acid at or adjacent to cells of the central nervous system tissue further comprises administering before or simultaneous with the delivery of nucleic acid to the central nervous system tissue a compound which causes hypersmolarity in the central nervous system tissue.

* * * * *